(12) United States Patent
Miller

(10) Patent No.: US 12,414,677 B2
(45) Date of Patent: *Sep. 16, 2025

(54) ENDOSCOPE ACCESSORY WITH LOCKING ELEMENTS

(71) Applicant: GI Scientific, LLC, Arlington, VA (US)

(72) Inventor: Scott Miller, Arlington, VA (US)

(73) Assignee: GI Scientific, LLC, Arlington, VA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/422,229

(22) Filed: Jan. 25, 2024

(65) Prior Publication Data

US 2024/0156332 A1 May 16, 2024

Related U.S. Application Data

(63) Continuation of application No. 17/572,850, filed on Jan. 11, 2022, now Pat. No. 11,910,999, which is a
(Continued)

(51) Int. Cl.
*A61B 1/00* (2006.01)
*A61B 1/018* (2006.01)
(Continued)

(52) U.S. Cl.
CPC ...... *A61B 1/00098* (2013.01); *A61B 1/00101* (2013.01); *A61B 1/00105* (2013.01); *A61B 1/00131* (2013.01); *A61B 1/00137* (2013.01); *A61B 1/00142* (2013.01); *A61B 1/00177* (2013.01); *A61B 1/018* (2013.01);
(Continued)

(58) Field of Classification Search
CPC ............ A61B 1/00098; A61B 1/00089; A61B 1/00133; A61B 1/00137; A61B 1/01; A61B 1/018
See application file for complete search history.

(56) References Cited

U.S. PATENT DOCUMENTS 3,774,614 A 11/1973 Cook
3,858,577 A 1/1975 Bass et al.
(Continued)

FOREIGN PATENT DOCUMENTS

CN 1692872 A 11/2011
DE 3532609 A 3/1987
(Continued)

OTHER PUBLICATIONS

European Examination Report for EP Appl. No. 15843356.5 dated May 20, 2019, 7 pages.
(Continued)

*Primary Examiner* — Aaron B Fairchild
(74) *Attorney, Agent, or Firm* — Farber LLC

(57) ABSTRACT

An endoscope accessory, such as a coupler device, is provided that includes a main body with a visualization section for allowing viewing of tissue by the endoscope and a proximal end configured for attachment to a distal end portion of the endoscope. The device includes a passage within the main body having an open distal end and a proximal end aligned with the working channel of the endoscope. A locking element on the coupler device secures an angle of exit of an instrument passing through the passage.

9 Claims, 17 Drawing Sheets

Related U.S. Application Data continuation of application No. 16/897,098, filed on Jun. 9, 2020, now Pat. No. 11,253,137, which is a continuation of application No. 15/746,196, filed as application No. PCT/US2016/433721 on Jul. 21, 2016, now Pat. No. 10,856,724.

(60) Provisional application No. 62/195,291, filed on Jul. 21, 2015.

(51) Int. Cl.
  *A61B 1/06* (2006.01)
  *A61B 1/273* (2006.01)

(52) U.S. Cl.
  CPC .......... *A61B 1/0676* (2013.01); *A61B 1/2736* (2013.01); *A61B 1/00089* (2013.01); *A61B 1/00103* (2013.01); *A61B 1/00165* (2013.01); *A61B 1/00181* (2013.01)

(56) References Cited

U.S. PATENT DOCUMENTS

| | | |
|---|---|---|
| 4,090,501 A | 5/1978 | Chaitin |
| 4,201,199 A | 5/1980 | Smith |
| 4,207,872 A | 6/1980 | Meiri et al. |
| 4,340,811 A | 7/1982 | Yamashita et al. |
| 4,681,093 A | 7/1987 | Ono et al. |
| 4,696,544 A | 9/1987 | Costella |
| 4,744,620 A | 5/1988 | Ueno et al. |
| 4,779,611 A | 10/1988 | Grooters et al. |
| 4,805,598 A | 2/1989 | Ueda |
| 4,878,725 A | 11/1989 | Hessel et al. |
| 4,881,810 A | 11/1989 | Hasegawa |
| 4,888,243 A | 12/1989 | Jonas et al. |
| 4,967,732 A | 11/1990 | Inoue |
| 5,040,715 A | 8/1991 | Green et al. |
| 5,050,585 A | 9/1991 | Takahashi |
| 5,080,660 A | 1/1992 | Buelna |
| 5,104,025 A | 4/1992 | Main et al. |
| 5,137,198 A | 8/1992 | Nobis et al. |
| 5,201,900 A | 4/1993 | Nardella |
| 5,205,459 A | 4/1993 | Brinkerhoff et al. |
| 5,237,984 A | 8/1993 | Williams, III et al. |
| 5,271,379 A | 12/1993 | Phan et al. |
| 5,326,013 A | 7/1994 | Green et al. |
| 5,329,935 A | 7/1994 | Takahashi |
| 5,337,734 A | 8/1994 | Saab |
| 5,342,388 A | 8/1994 | Toller |
| 5,413,052 A | 5/1995 | Breezer et al. |
| 5,413,268 A | 5/1995 | Green et al. |
| 5,443,781 A | 8/1995 | Saab |
| 5,448,990 A | 9/1995 | De Faria-Correa |
| 5,460,168 A | 10/1995 | Masubuchi et al. |
| 5,476,206 A | 12/1995 | Green et al. |
| 5,536,236 A | 7/1996 | Yabe et al. |
| 5,555,129 A | 9/1996 | Konno et al. |
| 5,569,157 A | 10/1996 | Nakazawa et al. |
| 5,575,291 A | 11/1996 | Hayakawa et al. |
| 5,605,532 A | 2/1997 | Schermerhorn |
| 5,632,717 A | 5/1997 | Yoon |
| 5,657,921 A | 8/1997 | Young et al. |
| 5,662,258 A | 9/1997 | Knodel et al. |
| 5,674,181 A | 10/1997 | Iida |
| 5,707,342 A | 1/1998 | Tanaka |
| 5,725,474 A | 3/1998 | Yasui et al. |
| 5,725,475 A | 3/1998 | Yasui et al. |
| 5,738,629 A | 4/1998 | Moll et al. |
| 5,743,851 A | 4/1998 | Moll et al. |
| 5,771,327 A | 6/1998 | Bar-Or et al. |
| 5,788,628 A | 8/1998 | Matsuno et al. |
| 5,808,813 A | 9/1998 | Lucey et al. |
| 5,840,014 A | 11/1998 | Miyano et al. |
| 5,860,913 A | 1/1999 | Yamaya et al. |
| 5,897,487 A | 4/1999 | Ouchi |
| 5,916,148 A | 6/1999 | Tsuyuki |
| 6,059,719 A | 5/2000 | Yamamoto et al. |
| 6,131,789 A | 10/2000 | Schulze et al. |
| 6,217,509 B1 | 4/2001 | Foley et al. |
| 6,250,532 B1 | 6/2001 | Green et al. |
| 6,277,065 B1 | 8/2001 | Donofrio |
| 6,283,951 B1 | 9/2001 | Flaherty et al. |
| 6,293,907 B1 | 9/2001 | Axon et al. |
| 6,306,081 B1 | 10/2001 | Ishikawa et al. |
| 6,409,725 B1 | 6/2002 | Khandkar et al. |
| 6,416,462 B1 | 7/2002 | Tovey et al. |
| 6,673,091 B1 | 1/2004 | Shaffer et al. |
| 6,689,130 B2 | 2/2004 | Arai et al. |
| 6,699,180 B2 | 3/2004 | Kobayashi |
| 6,712,524 B2 | 3/2004 | Beatty et al. |
| 6,723,350 B2 | 4/2004 | Burrell et al. |
| 6,733,440 B2 | 5/2004 | Ailinger et al. |
| 6,770,069 B1 | 8/2004 | Hobart et al. |
| 6,792,837 B2 | 9/2004 | Battistone |
| 6,855,108 B2 | 2/2005 | Ishibiki et al. |
| 6,866,627 B2 | 3/2005 | Nozue |
| 6,934,093 B2 | 8/2005 | Kislev et al. |
| 6,981,628 B2 | 1/2006 | Wales |
| 6,988,650 B2 | 1/2006 | Schwemberger et al. |
| 7,033,317 B2 | 4/2006 | Pruitt |
| 7,046,439 B2 | 5/2006 | Kaminsky et al. |
| 7,087,012 B2 | 8/2006 | Ishibiki |
| 7,112,195 B2 | 9/2006 | Boll et al. |
| 7,205,339 B2 | 4/2007 | Muratoglu |
| 7,235,592 B2 | 6/2007 | Muratoglu et al. |
| 7,238,153 B2 | 7/2007 | Moriyama |
| 7,245,813 B2 | 7/2007 | Brown et al. |
| 7,464,847 B2 | 12/2008 | Viola et al. |
| 7,537,561 B2 | 5/2009 | Yamaya et al. |
| 7,553,278 B2 | 6/2009 | Kucklick |
| 7,554,743 B2 | 6/2009 | Jiang et al. |
| 7,566,993 B2 | 7/2009 | May |
| 7,621,868 B2 | 11/2009 | Breidenthal et al. |
| 7,819,872 B2 | 10/2010 | Johnson et al. |
| 7,977,255 B1 | 7/2011 | Scheer et al. |
| 8,180,423 B2 | 5/2012 | Mang et al. |
| 8,241,204 B2 | 8/2012 | Spivey |
| 8,905,921 B2 | 12/2014 | Titus |
| 8,915,931 B2 | 12/2014 | Boudreaux et al. |
| 9,459,442 B2 | 10/2016 | Miller |
| 9,709,795 B2 | 7/2017 | Miller |
| 10,101,574 B2 | 10/2018 | Miller |
| 2002/0035311 A1 | 3/2002 | Ouchi |
| 2002/0065515 A1 | 5/2002 | Falwell et al. |
| 2002/0133148 A1 | 9/2002 | Daniel et al. |
| 2003/0040657 A1 | 2/2003 | Yamaya et al. |
| 2003/0181900 A1 | 9/2003 | Long |
| 2004/0157073 A1 | 8/2004 | Burrell et al. |
| 2004/0249246 A1 | 12/2004 | Campos |
| 2004/0263613 A1 | 12/2004 | Morita |
| 2004/0267092 A1 | 12/2004 | Ishibiki |
| 2005/0043589 A1 | 2/2005 | Pruitt |
| 2005/0080411 A1 | 4/2005 | Ouchi |
| 2005/0131279 A1 | 6/2005 | Boulais et al. |
| 2005/0197530 A1 | 9/2005 | Wallace et al. |
| 2005/0234297 A1 | 10/2005 | Devierre et al. |
| 2006/0030844 A1 | 2/2006 | Knight et al. |
| 2006/0084839 A1 | 4/2006 | Mourlas et al. |
| 2006/0173241 A1 | 8/2006 | Ouchi et al. |
| 2006/0200176 A1 | 9/2006 | Matsuno et al. |
| 2006/0229662 A1 | 10/2006 | Finkielsztein et al. |
| 2006/0270900 A1 | 11/2006 | Chin et al. |
| 2006/0270978 A1 | 11/2006 | Binmoeller |
| 2007/0038043 A1 | 2/2007 | Gelikonov et al. |
| 2007/0066869 A1 | 3/2007 | Hoffman |
| 2007/0066870 A1 | 3/2007 | Ohashi et al. |
| 2007/0073108 A1 | 3/2007 | Takahashi |
| 2007/0208219 A1 | 9/2007 | Carter |
| 2007/0239620 A1 | 10/2007 | Schwartz et al. |
| 2007/0249898 A1 | 10/2007 | Otawara |
| 2007/0260117 A1 | 11/2007 | Zwolinski et al. |
| 2007/0270897 A1 | 11/2007 | Skerven |
| 2007/0282256 A1 | 12/2007 | Hu et al. |
| 2007/0293888 A1 | 12/2007 | Harren et al. |

(56) References Cited

U.S. PATENT DOCUMENTS

| | | |
|---|---|---|
| 2008/0021268 A1 | 1/2008 | Shoroji et al. |
| 2008/0021269 A1 | 1/2008 | Tinkham et al. |
| 2008/0033246 A1 | 2/2008 | Matsui et al. |
| 2008/0139885 A1 | 6/2008 | Knapp |
| 2008/0177135 A1 | 7/2008 | Muyari et al. |
| 2008/0188874 A1 | 8/2008 | Henderson |
| 2008/0262295 A1 | 10/2008 | Kendale et al. |
| 2008/0306335 A1 | 12/2008 | Lau et al. |
| 2009/0048483 A1 | 2/2009 | Yamamoto |
| 2009/0048486 A1 | 2/2009 | Surti |
| 2009/0062790 A1 | 3/2009 | Malchano et al. |
| 2009/0098409 A1 | 4/2009 | Yamada et al. |
| 2009/0124858 A1 | 5/2009 | Oskin et al. |
| 2009/0143643 A1 | 6/2009 | Weitzner et al. |
| 2009/0156898 A1 | 6/2009 | Ichimura |
| 2009/0254164 A1 | 10/2009 | Johnson et al. |
| 2009/0315989 A1 | 12/2009 | Adelson |
| 2009/0326328 A1 | 12/2009 | Kucklick |
| 2010/0026940 A1 | 2/2010 | Takegami et al. |
| 2010/0121442 A1 | 5/2010 | Shea et al. |
| 2010/0017414 A1 | 7/2010 | Hsu |
| 2010/0203454 A1 | 8/2010 | Brongersma et al. |
| 2010/0268027 A1 | 10/2010 | Aono et al. |
| 2010/0286475 A1 | 11/2010 | Robertson |
| 2011/0124960 A1 | 5/2011 | St. Onge et al. |
| 2011/0152618 A1 | 6/2011 | Surti |
| 2011/0241460 A1 | 10/2011 | Jiang |
| 2012/0034573 A1 | 2/2012 | Erdmann et al. |
| 2012/0209074 A1 | 8/2012 | Titus |
| 2012/0209090 A1 | 8/2012 | Goodall et al. |
| 2012/0232342 A1 | 9/2012 | Reydel |
| 2013/0040516 A1 | 2/2013 | Pruneri et al. |
| 2013/0090527 A1 | 4/2013 | Axon |
| 2013/0144287 A1 | 6/2013 | Crowley et al. |
| 2013/0190562 A1 | 7/2013 | Smith et al. |
| 2013/0237998 A1 | 9/2013 | Wallace et al. |
| 2014/0027578 A1 | 1/2014 | Comtesse |
| 2015/0065795 A1 | 3/2015 | Titus |
| 2015/0073214 A1 | 3/2015 | Ueda |
| 2016/0029875 A1 | 2/2016 | Okada |
| 2016/0051135 A1 | 2/2016 | Greenberg et al. |
| 2016/0270636 A1 | 9/2016 | Iwasaka et al. |
| 2017/0066111 A1 | 3/2017 | Wang |
| 2017/0251910 A1 | 9/2017 | Surti et al. |
| 2017/0311789 A1 | 11/2017 | Mulcahey et al. |
| 2017/0311974 A1 | 11/2017 | Friedrichs |
| 2018/0160886 A1 | 6/2018 | Govani et al. |
| 2018/0206708 A1 | 7/2018 | Miller |
| 2019/0009963 A1 | 1/2019 | Wessely |
| 2019/0070998 A1 | 3/2019 | Spencer et al. |
| 2020/0100655 A1 | 4/2020 | Morishima et al. |

FOREIGN PATENT DOCUMENTS

| | | |
|---|---|---|
| EP | 1870018 A2 | 12/2007 |
| JP | H0373168 A | 3/1991 |
| JP | 07178094 | 7/1995 |
| JP | H09238893 A | 9/1997 |
| JP | 05123288 | 5/1999 |
| JP | 2000300570 A | 10/2000 |
| JP | 3124079 B2 | 1/2001 |
| JP | 200217655 | 1/2002 |
| JP | 2002233491 A | 8/2002 |
| JP | 2003033319 A | 2/2003 |
| JP | 2003339631 A | 12/2003 |
| JP | 2005066139 A | 3/2005 |
| JP | 2006026344 A | 2/2006 |
| JP | 2008029384 | 2/2008 |
| JP | 2009261830 A | 11/2009 |
| JP | 2010063721 | 3/2010 |
| WO | WO 9929362 A1 | 6/1999 |
| WO | WO 2001085319 A1 | 11/2001 |
| WO | WO 2006138409 A2 | 12/2006 |
| WO | WO 2007029230 A2 | 3/2007 |
| WO | WO 2007029814 A1 | 3/2007 |
| WO | WO 2007147060 A2 | 12/2007 |
| WO | WO 2009149042 A2 | 12/2009 |
| WO | WO 2011085319 A1 | 7/2011 |
| WO | WO 2011099329 A1 | 8/2011 |
| WO | WO 2011148172 A2 | 12/2011 |
| WO | WO 2014123563 A1 | 8/2014 |
| WO | WO 2017011535 A1 | 1/2017 |

OTHER PUBLICATIONS

Extended European Search Report for EP Appl. No. 16828548.4 dated Feb. 28, 2019.

Extended European Search Report for EP Appl. No. 16804476.6 dated Dec. 5, 2018.

Extended European Search Report and Written Opinion for EP Appl. No. 16804462-6 dated Dec. 10, 2018.

Extended European Search Report for EP Appl. No. 12747511.9 dated Jan. 3, 2018.

Extended European Search Report for EP Appl. No. 18174913.6 dated Aug. 16, 2019.

International Preliminary Report on Patentability issued in PCT/US2015/051662 dated Apr. 6, 2017.

International Search Report and Written Opinion for PCT Appl. No. PCT/US2019/012448 mailed Apr. 16, 2019.

International Search Report and Written Opinion dated Oct. 26, 2016 for PCT Application No. PCT/US2016/043371, filed Jul. 21, 2016.

International Search Report issued in corresponding International Application No. PCT/US2015/051662 dated Dec. 14, 2015.

International Search Report and Written Opinion dated Sep. 21, 2012 for PCT Appl. No. PCT/US2012/025404.

Japanese Patent Office, Notification of Reasons for Refusal, JP Appl. No. 2013-554596, Dec. 8, 2015.

Chinese Office Action and Search Report for CN Appl. No. 201280014363, Mar. 23, 2015.

Chinese Office Action for CN Appl. No. 201280014363, Jan. 5, 2016.

Chinese Office Action for CN Appl. No. 201680045602.6 dated Jun. 5, 2019.

First Examination Report for Indian Appl. No. 6566/CHENP/2013 dated Aug. 29, 2019.

Beneq Biocompatible Coatings Webpage.

Cargille Laboratories, Inc. Material Safety Data Sheet—Cargille Optical Gel Code 0607, Jun. 3, 2005.

Depth of Field, OPMI Application Tip #2, Informed for Medical Professionals in Neuro, ENT and Spine, 2nd Issue, Oct. 2006, Published by Carl Zeiss Surgical GmbH, Germany.

Jaxton, et al., An Experimental Investigation on the Development of Hydrogels for Optical Applications, Polymer Testing, 2003, 22(4):371-374, English Abstract.

Kopp, et al., Chapter 9, Optical Principles of the Endoscope, Hysteroscopy: Visual Perspectives of Uterine Anatomy, Physiology & Pathology, 3rd Edition, Lippincott Williams & Wilkins, 2007, 19 pages.

Maquet Training Manual, Vasoview 6 Endoscopic Vessel Harvesting System, Cardiovascular, Copyright Maquet Cardiovascular LLC, Oct. 2008.

Oil Immersion, From Wikipedia, http://en.wikipedia.org/wiki/Oil.sub.--immerson, Printed Sep. 7, 2010.

Olympus Colonoscopes Outpatient Doctor Surgery Center, http://outpatientsurgicare.com/index.PHP?Facilities: Technologies:Olympus.sub.--Colonoscopes&print, Printed Oct. 26, 2010.

Olympus Disposal Distal Attachment Product Data Sheet.

Olympus Evis Exera Colonovideoscope/Sigmoidovideoscope, Olympus CF Type Q1601JUS, Today's Most Versatile Choice for Colonoscopy, Product Data Sheet.

Olympus Technologies Evis Exera II, Learn About Wide—Angle, http://www.olympusamerica.com/msg.sub.--section/msg.sub.--endoscopy.sub.---technology.asp, Copyright 2010 Olympus America Inc.

(56) References Cited

OTHER PUBLICATIONS

Olympus Technologies Evis Exera II, Learn About Close Focus, http://www.olympusamerica.com/msg.sub.--section/msg.sub.--endoscopy.sub.---technology.asp, Copyright 2010 Olympus America Inc.

Olympus NA-11J-KB Product Data Sheet.

Optical Gels for Fiber-Optic Connectors and Splices—A Tutorial, Nye Optical Products, 6 pages.

Paxton, et al., An Experimental Investigation on the Development of Hydrogels for Optical Applications, Polymer Testing, 2003, 22(4):371-374, English Abstract.

Sigma-Aldrich Poly(2-hydroxyethyl methacrylate) Product Data Sheet, http://www.sigmaaldrich.com/catalog/ProductDetail, Copyright 2010 Sigma-Aldrich Co.

Sigma-Aldrich Poly(ethylene glycol) Product Data Sheet, http://www.sigmaaldrich.com/catalog/ProductDetail, Copyright 2010 Sigma-Aldrich Co.

Sigma-Aldrich Poly(vinyl alcohol) Product Data Sheet, http://www.sigmaaldrich.com/catalog/ProductDetail, Copyright 2010 Sigma-Aldrich Co.

Sigma-Aldrich Methacrylic acid Product Data Sheet, http://www.sigmaaldrich.com/catalog/ProductDetail, Printed Sep. 3, 2010.

SmartGel Nye Nyogel OCK-451LPH Product Data Sheet, Nye Optical Products.

Smeds, et al., Photocrosslinkable Polysaccharides for in situ Hydrogel Formation, Journal of Biomedical Materials Research, 2001, 54:115-121.

Stadler, Transparent conducting oxides—An up-to-date overview, Materials 5.4:661-683, 2012.

The Basics of Silicon Chemistry, Basic Silicon Production and Siloxane Polymerization, http://www.dowcorning.com/content/sitech/sitechbasics/siloxane.sub.--poly-merization.asp, Copyright 2000-2010 Dow Corning Corporation.

Uw Eye Research Institute, Newsletter, Point of View, Summer 2009, http://vision.wisc.edu/news.sub.--sum09.html, Printed Feb. 5, 2010.

Vinyl Sustainability Forum 2014, Title: Benefits of PVC, Date retrieved: Mar. 7, 2014 from website: http://www.pvc.org/en/p/benefits-of-pvc, pp. 1-4.

Zeng, et al., An Endoscope Utilizing Tunable-Focus Microlenses Actuated through Infrared Light, Solid-State Sensors, Actuators and Microsystems Conference, 2009, Transducers 2009, International, Issue 21-25, pp. 1214-1217, Abstract Only.

Zeng, et al., Tunable Liquid Microlens Actuated by Infrared Light-Responsive Hydrogel, Applied Physics Letters, 2008, 93:151101-1-151101-3.

Republic of China Patent Office; Office Action; Chinese Patent Application No. 201680054885.0; Jun. 3, 2020.

International Search Report and Written Opinion dated Dec. 16, 2020 for PCT Appl. No. PCT/US2020/65429.

International Search Report and Written Opinion dated Dec. 16, 2020 for PCT Appl. No. PCT/US2020/65424.

International Search Report and Written Opinion dated Dec. 16, 2020 for PCT Appl. No. PCT/US2020/65427.

International Preliminary Report on Patentability; PCT/US2021/026528; GI Scientific, LLC; Oct. 20, 2022.

ENDOSCOPE ACCESSORY WITH LOCKING ELEMENTS

CROSS-REFERENCE TO RELATED APPLICATIONS

This application is a continuation of U.S. patent application Ser. No. 17/572,850, filed Jan. 11, 2022, which is a continuation of U.S. patent application Ser. No. 16/897,098 filed Jun. 9, 2020, issued as U.S. Pat. No. 11,253,137 on Feb. 22, 2022, which is a continuation of U.S. patent application Ser. No. 15/746,196 filed Jan. 19, 2018, issued as U.S. Pat. No. 10,856,724 on Dec. 8, 2020, which claims priority to International Patent Application Serial No. PCT/US16/43371, filed Jul. 21, 2016, which claims the benefit of U.S. Provisional Application No. 62/195,291, filed Jul. 21, 2015, all of which are hereby incorporated by reference for all purposes as if copied and pasted herein.

FIELD

The present disclosure relates to a medical device, and more particularly to a device for covering and extending a working end portion of an optical imaging endoscope. The device provides a flexible working channel extension in communication with the working channel of the endoscope so that instruments can exit out of the working end portion at various angles, while also protecting the working end portion from ingress of bacteria, tissue, fluid, and other debris which could lead to infection and decreased performance of the scope.

BACKGROUND

Recent advances in optical imaging technology have allowed many medical procedures to be performed today in a minimally invasive manner. The evolution of the more sophisticated, flexible scope with advanced visual capabilities has allowed access to regions deep within the human body that could only be achieved before with invasive surgical intervention. This modem day convenience has resulted in an increase in the demand for, as well as the number of, endoscopic, laparoscopic, arthroscopic, ophthalmoscopic, borescopic, or other remote imaging visualization procedures performed every year in the U.S. While these procedures are relatively safe, they are not without risks.

Endoscopy, for instance, is a procedure in which a lighted visualization device called an endoscope is inserted into the patient's body to look inside a body cavity or organ for the purpose of examination, diagnosis or treatment. The endoscope may be inserted through a small incision or through a natural opening of the patient. In a bronchoscopy, the endoscope is inserted through the mouth, while in a sigmoidoscopy, the endoscope is inserted through the rectum. Unlike most other medical imaging devices, endoscopes are inserted directly into the organ.

Today, most endoscopes are reused. This means that, after an endoscopy, the endoscope goes through a cleaning, disinfecting or sterilizing, and reprocessing procedure to be introduced back into the field for use in another endoscopy on another patient. In some cases, the endoscope is reused several times a day on several different patients.

While the cleaning, disinfecting and reprocessing procedure is a rigorous one, there is no guarantee that the endoscopes will be absolutely free and clear of any form of contamination. Modern day endoscopes have sophisticated and complex optical visualization components inside very small and flexible tubular bodies, features that enable these scopes to be as effective as they are in diagnosing or treating patients. However, the trade off for these amenities is that they are difficult to clean because of their small size, and numerous components. These scopes are introduced deep into areas of the body which expose the surfaces of these scopes to elements that could get trapped within the scope or adhere to the surface, such as body fluids, blood, and even tissue, increasing the risk of infection with each repeated use.

Endoscopes used in the gastrointestinal tract, especially specialty endoscopes also known as duodenoscopes with a side-viewing capability, have an added complexity in that they are in a bacteria rich environment. Typical duodenoscopes have internal moving components like an elevator with hinges attached to a cable for actuation. The elevator is used to deflect and therefore change the direction of instruments passed down the scope's working channel. This elevator is beneficial in that it can allow the user to change the direction of a wire or a catheter to direct the wire or catheter into a specific opening, so that one or more instruments can be turned to enter a particular body lumen. However, given the size, location and movement of the elevator during use, the elevator creates cleaning issues, including the risk that bacteria finds its way into the elevator's hinges and other hard to clean locations on the scope. This provides an opportunity for bacteria to colonize and become drug resistant, creating the risk of significant illness and even death for a patient. This infection risk is also present in the cable mechanisms that are used to move the elevator mechanism back and forth and in other aspects of current scope designs. Moreover, in addition to the health risks posed by bacterial contamination, the accumulation of fluid, debris, bacteria, particulates, and other unwanted matter in these hard to clean areas of the scope also impact performance, shortening the useful life of these reusable scopes.

Accordingly, it is desirable to provide devices which serve as convenient accessories for currently existing endoscopes to reduce the risk of contamination and infection, while also improving the performance of the endoscope. It is particularly desirable to provide an accessory for a duodenoscope that allows the user simultaneously to protect the working end from bacterial contamination and also enable instruments to exit out of the working end of the scope at different angles with ease.

SUMMARY

The present disclosure provides a coupler device for covering and sealing a portion of the working end of a side viewing endoscope, with a flexible and tubular working channel extension that extends the working channel of the scope and can be angularly adjustable. The coupler device protects the scope and its components, particularly the scope elevator, to reduce the risk of debris, fluid and other matter ending up in the elevator and behind the elevator and the working channel, potentially causing infection risk and, in some embodiments, the device has its own way to articulate instruments, eliminating the need to have a scope with an elevator. The device may be single use disposable or reusable.

The coupler device may be provided as a single-use disposable accessory to an endoscope that provides the user with the ability to change the angle of exit of a device being advanced out of the working channel of an endoscope, without exposing the distal end of the scope to bacteria, debris, fluid and particulate matter. In some embodiments, the device attaches to the end of the endoscope and covers the working channel of the endoscope with a working channel extension in the coupler device, allowing an instrument to be passed down the working channel of the endoscope and into the working channel extension of the coupler device. The working channel extension can provide a seal against the scope working channel, so instruments can be passed back and forth through the scope working channel and out the working channel extension of the coupler device without fluid and bacteria entering areas outside of the scope working channel. This seal is accomplished, in some embodiments, through an extension of the device working channel into the scope working channel, through a gasket on the end of the working channel extension, by way of a temporary glue, through pressure and the seal of the overall device against the distal end of the scope, through the selection of elastic and elastomeric materials, and other suitable and alternative means.

The working channel extension of the coupler device can be made of one or more materials with elastic properties. The materials can include biocompatible material(s) when the device is intended for medical applications, which may include, without limitation, elastic and elastomeric materials, as well as combinations of rigid and flexible materials, including silicone joined to polycarbonate and other materials joined to a biocompatible metal.

In some embodiments, the working channel extension of the coupler device may include an elastic biocompatible material that reduces the friction involving in passing devices through the working channel extension, which is joined to a biocompatible metal, such as a coil spring, an additional elastic material that is joined to the biocompatible metal, to improve flexibility, reduce kinking and aid in sealing the working channel of the device against the endoscope's working channel.

In some embodiments, the device allows the user to articulate the working channel of the device in the direction preferred by the user of the endoscope, so that a wire, catheter or other instrument being advanced down the working channel of the endoscope can direct the wire or catheter or other instrument in a preferred direction different than the angle at which the instrument would exit the endo scope if the coupler device was not in place or if an elevator in the scope is not used. This redirection of an instrument has the benefit of assisting with the navigation of the device, while not allowing fluid, debris, particulate matter, bacteria and other unwanted elements to enter hard to clean areas of the endo scope, especially at the distal end of the endoscope.

The benefits of the invention include allowing the physician to change the angle of exit, so that one or more devices can be turned to enter a particular body lumen, such as a biliary duct or pancreatic duct, or other hard to reach area, including in non-medical procedures, while sealing the distal end of the scope to prevent infection and the intrusion of debris and particulate matter into interior elements of the scope that are hard to reach to effectively clean.

In some embodiments, the device may be formed of an optically clear material that covers the end of the endoscope and seals the end of the endoscope, allowing visualization of the endoscope's camera without obscuring the view by the device. The optically clear material may also cover the endoscope's light guide to allow the light projected by the endoscope to illuminate the field of view of the endo scope. In some embodiments, the optically clear material may include navigation markers to orient the user when visualizing tissue, such as markers to identify the relative position of the scope as the user visualizes the tissue through the optically clear material.

In embodiments, the optically clear material may also include other markers to guide the user with confirmation of the accurate placement of the optically clear material over the endoscope's camera and, if applicable, over the endoscope's light guide.

In some embodiments, the device may articulate instruments through the device through a cable in a sealed sheath that is attached to the flexible working channel extension in the coupler device, allowing the user to advance and retract the cable to move the working channel extension backward and forward to change the angle of exit from the flexible working channel in order to direct an instrument to a desired direction.

In some embodiments, the device may have multiple cables so the angle of exit can be articulated in multiple directions, including in different quadrants, unlike with the current endoscope elevators, which can only deflect and therefore redirect an instrument in a single axis due to the limited travel of endoscope elevators, which can only be raised or lowered, but not moved from side to side or articulated into other quadrants. In some embodiments, the cable(s) may be attached directly to the working channel extension or to other devices that can be articulated and cause the working channel extension to change its angle of exit, including, for example, a dowel underneath the working channel extension, but encased in the device that can be advanced forward and backward to move the working channel extension as the cable is advanced and retracted. In some embodiments, the articulation ability of the coupler device may be created with an elevator embedded in the coupler device, which is disposable and therefore thrown away after the procedure.

The articulation ability of the coupler device may also take place with elements that do not involve cables, including for example, piezo electric materials, micro motors, organic semiconductors, and electrically activated polymers. In some embodiments, the articulation ability of the coupler device may also take place with the transfer of force to the working channel extension or an embedded elevator through interlocking connectors that transfer force, wires that twist, slidable sheaths, and memory metals that change shape through the transfer of temperature. In some embodiments, the device includes a power connector or motors to deliver energy, including electromagnetic energy, to the device to cause a transfer in force to change the angle of exit from the coupler device as an instrument is passed through the device, or in advance of passing an instrument through the device. This transfer of force can include causing the device to rotate as it exits the working channel extension. The device may be navigated and articulated by the user directly, or as part of a robotic system in which the users input is translated through the system through various means, including cables, power connectors, motors, electromagnetic energy, slideable sheaths, haptics, computer-guided and directed input, and other means to direct and guide the device to its intended location, including to specific diagnosis and treatment objectives in a patient, or in non-medical applications, to a desired remote location.

In some embodiments, the device may be integrated into a scope and configured to be detachable and reusable for separate cleaning, including manual cleaning, in an autoclave, an ETO sterilizer, gamma sterilizer, and other sterilization methods.

The articulation aspect of the coupler device may include a locking feature or capability to affix the angle of exit in the working channel extension at a specific angle. In some embodiments, the specific angle of exit may be aimed at a specific point in the gastrointestinal tract, such as a biliary or pancreatic duct, or the angle of exit may be affixed so that a wire or other instrument inside the working channel temporarily cannot be advanced, locking the instrument in position temporarily to aid in the exchange of instruments or to improve navigation of the instrument temporarily.

The device may include a disposable or reusable control mechanism that attaches to the endoscope to articulate the distal end of the coupler device to change the angle of exit from the working channel extension of the coupler device. In some embodiments, this control mechanism may also lock the angle of exit of the working channel extension or the working channel extension may be locked through elements in the endoscope itself, such as the elements that articulate the endoscope's elevator.

In some embodiments, the coupler device may cover the entire distal end of the endoscope, or may just cover hard to clean areas. In some embodiments, the coupler device may cover the distal end of the endoscope, or a portion thereof, or it may include a sheath attached to the coupler device which covers the entirety of the scope that is exposed to fluid, debris, particulate matter, bacteria and other unwanted elements.

In some embodiments, the device includes an anti-infective material. In another exemplary embodiment, the device includes an anti-infective coating. In still another embodiment, the device includes a coating that is hydrophobic. In yet another embodiment, the device is superhydrophobic. In even still another embodiment, the device is anti-infective and hydrophobic. Further yet in another embodiment, the device is anti-infective and superhydrophobic. In further still another exemplary embodiment, anti inflammatory coatings are incorporated into the device.

The device may include a silver ion coating and a silver hydrogel applied, infused or made part of the device in the area that covers or goes around the scope elevators. The device may also include a valve or other element at the distal end of the catheter channel and may in embodiments have a valve in the working channel extension to prevent having fluid and debris traveling from the lumen back into the scope working channel.

The device may include an electrical wire or other power transmission point to enable the creation of an electrical field across a silver ion coating to improve the activity of the silver ion coating or other coating to prevent infection.

It is to be understood that both the foregoing general description and the following detailed description are exemplary and explanatory only and are not restrictive of the disclosure. Additional features of the disclosure will be set forth in part in the description which follows or may be learned by practice of the disclosure.

BRIEF DESCRIPTION OF THE DRAWINGS

The accompanying drawings, which are incorporated in and constitute a part of this specification, illustrate several embodiments of the disclosure and together with the description, serve to explain the principles of the disclosure.

DETAILED DESCRIPTION

Figures 1A, 1B:
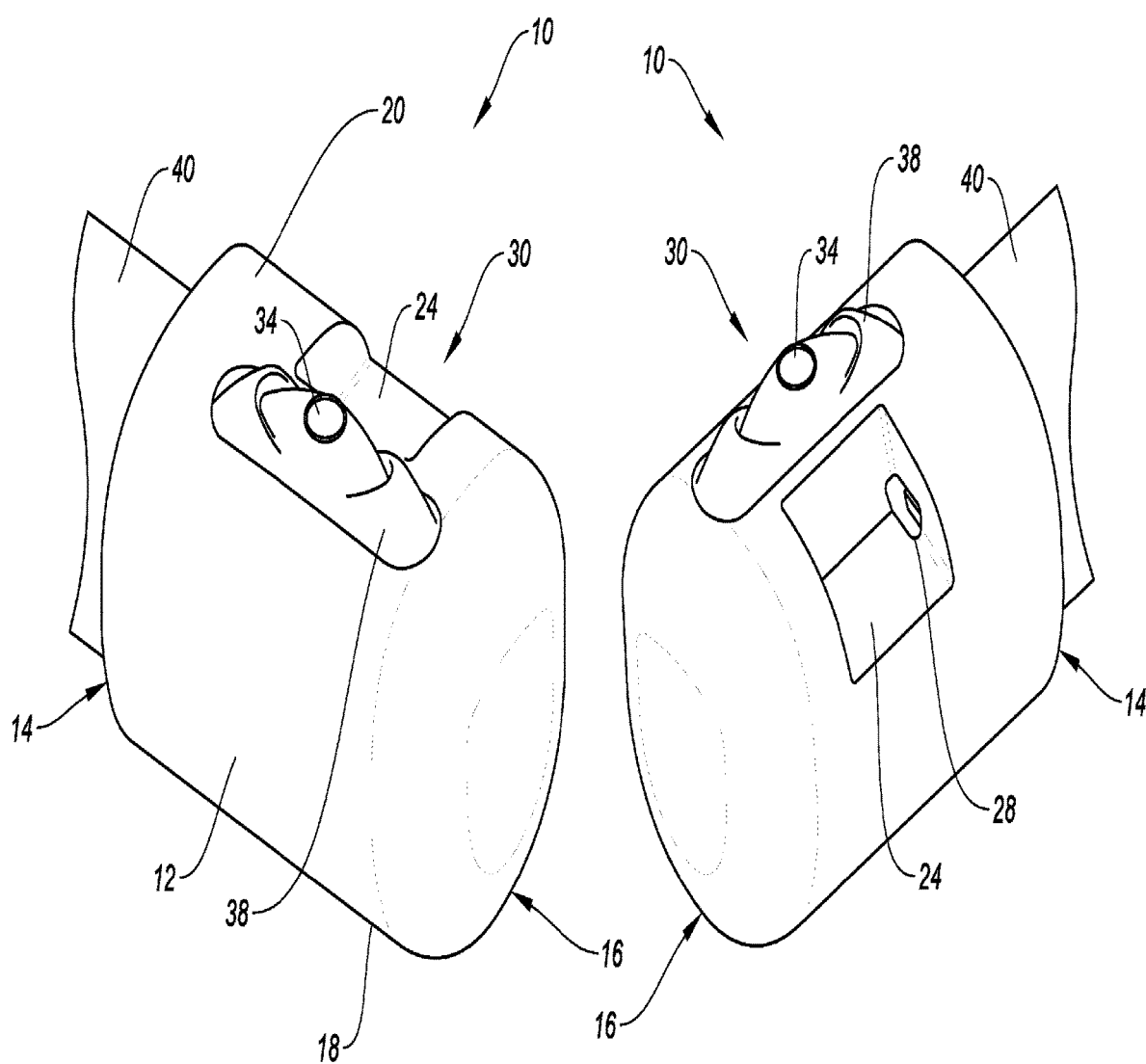
FIGS. 1A AND 1B are isometric views of an exemplary embodiment of the coupler device of the present disclosure in use with a duodenum scope.

Turning now to the drawings, FIGS. 1A and 1B illustrate an exemplary embodiment of a coupler device 10 of the present disclosure. The coupler device 10 serves as an accessory component for currently existing endoscopes. The device seals and covers infection prone areas of the scope to prevent ingress of debris, fluid, or other unwanted matter that could lead to bacterial contamination and decreased performance of the scope. In addition, the coupler device 10 provides a flexible working channel for instruments to be inserted into the scope. The flexible working channel can be angularly adjustable with ease. As shown, the coupler device 10 may be used with a duodenum scope 40 or other side-viewing scope instrument. It is understood, of course, that the coupler device 10 may be adapted for use with end viewing scopes as well. In addition, the coupler device 10 of the present disclosure can be used with all types of scopes for different medical applications. The duodenum scope 40 shown here is merely for illustrative purposes.

As FIGS. 1A and 1B illustrate, the coupler device 10 may comprise a main body 12, proximal end 14 and distal end 16, lower surface 18 and upper surface 20. The proximal end 14 attaches onto a working end of a duodenum scope 40, extending the working end portion of the scope 40. The upper surface 20 may include a lens and light guide 24 and a scope washer opening 28, which is used to push fluid across the scope camera to wash debris off the camera and is also used to push air across the camera to dry the camera and insufflate the patient's gastrointestinal tract. In addition, the upper surface 20 includes a flexible working channel region 30 that includes a flexible working channel extension 34 that is surrounded by a flexible membrane 38. This flexible membrane 38 serves as a protective hood or covering for the working end of the coupler device 10, providing for flexible articulation while sealing out debris, fluid, bacteria or other unwanted matter.

Figures 2A, 2B:
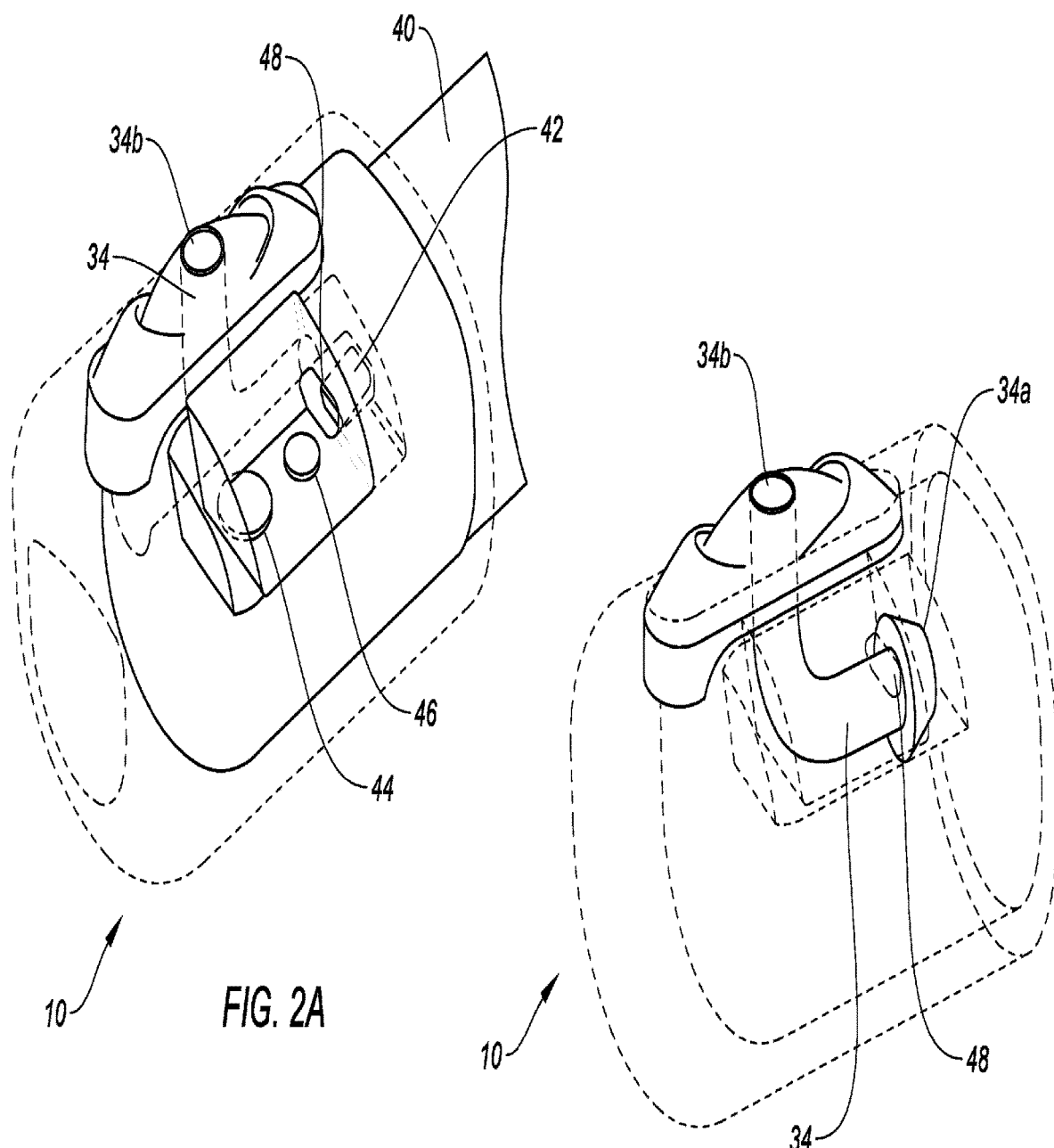
FIGS. 2A and 2B show partial cutaway views of the coupler device and a duodenum scope of FIGS. 1A AND 1B, respectively.
Figure 3:
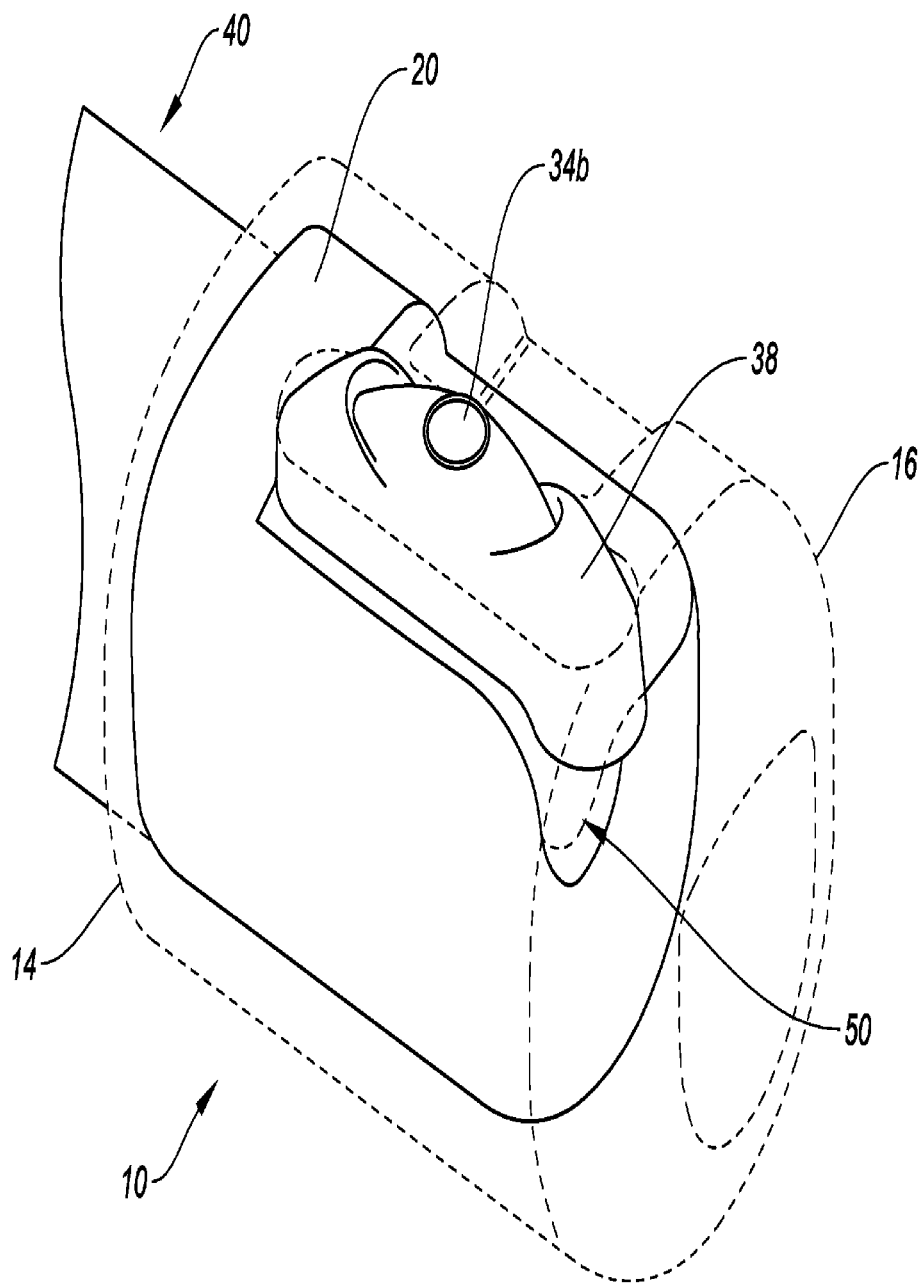
FIG. 3 shows another cutaway view of the coupler device and a duodenum scope of FIGS. 1A AND 1B.

As shown in FIGS. 2A and 2B, the duodenum scope 40 may comprise a light guide 44, lens 46 and washer opening 48. The coupler device 10 cooperates with each of these components of the scope 40 to provide a fully functioning scope. The coupler device 10 does not interfere with the scope's ability to emit a clear image, but instead reduces the risk of contamination with each use. This benefit is achieved by providing a coupler device 10 which attaches to the working end components of the scope 40, and seals around the working end.

Figure 4:
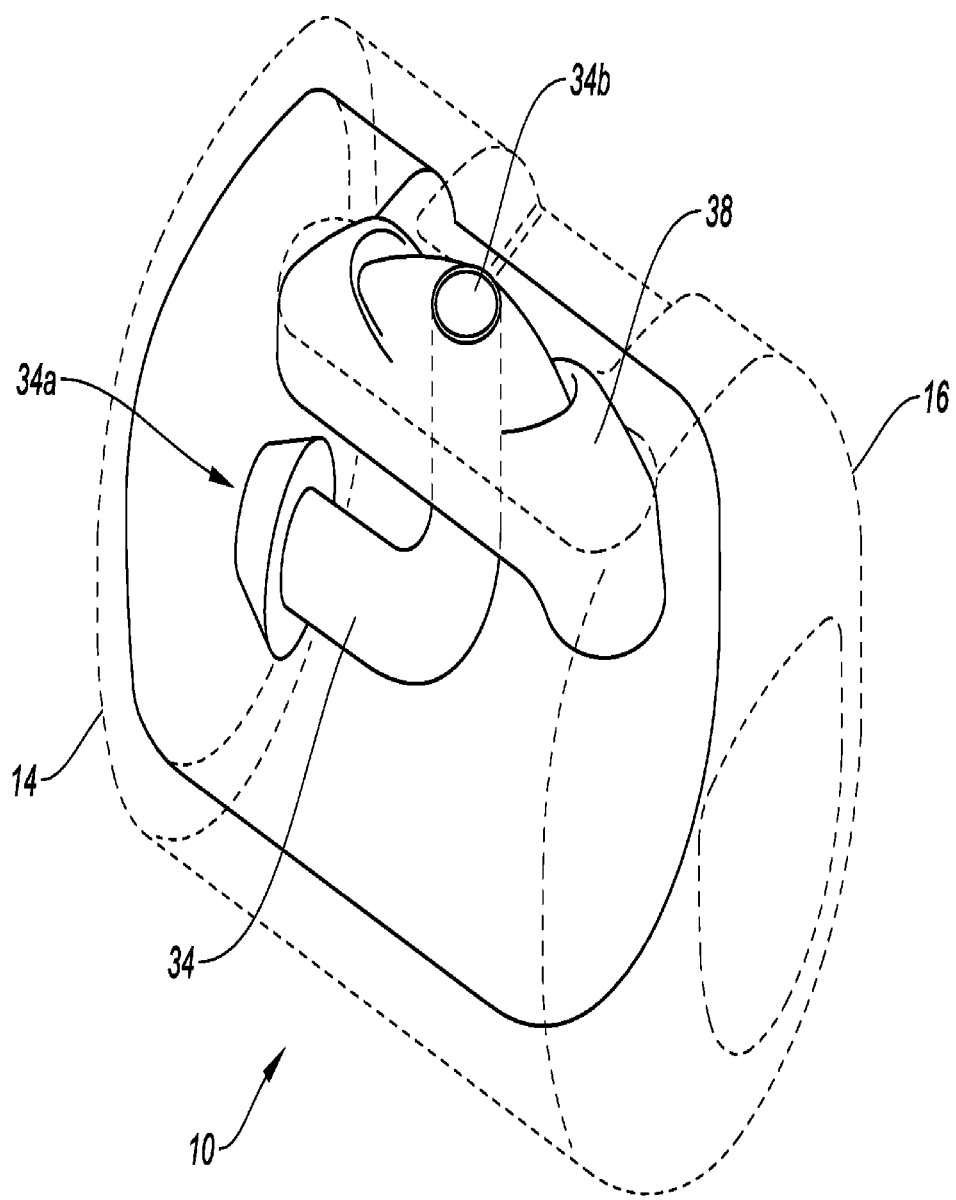
FIG. 4 shows still another cutaway view of the coupler device and a duodenum scope of FIGS. 1A AND 1B.

As further shown in FIGS. 1A, 1B 2A, 2B, 3 and 4, the coupler device 10 provides an extension of the scope's working channel 42. The working channel extension 34 of the coupler device 10 in FIG. 1 is flexible and may contact the scope's working channel 42 by a sealed connection, as shown in FIG. 4, at the proximal end 34a of the working channel extension. The distal end 34b of the working channel extension 34 serves as an exit portal for instruments to pass through the scope 40 to reach different areas of the body.

Additionally, the coupler device 10 provides a further seal around the elevator 50 of the scope. Because the coupler device 10 seals the elevator 40, risk of debris influx, fluids, bacteria and other matter build up behind the elevator and working channel is reduced significantly. This influx of debris, bacteria and other matter is believed to be the reason for drug resistant infections with current scopes today. While preventing influx, the coupler device 10 advantageously maintains flexibility to move the working channel extension 34.

In use, the scope's working channel extension 34 permits passage of instruments down the scope working channel 42 and through and out the working channel extension 34 of the device 40 for assessment and treatment of tissue and other matter. Such instruments may include cannula, catheters, stents and stent delivery systems, papillotomes, wires, other imaging devices including mini-scopes, baskets, snares and other devices for use with a scope in a lumen. This working channel extension 34 is flexible enough that the elevator 50 of the scope 40 can raise and lower the working channel extension 34 so that instruments can be advanced down and out of the working channel extension distal end (or exit portal) 34b of the scope 40 at various angles, or be raised and lowered by a cable or other means to articulate the working channel extension 34.

Figure 5:
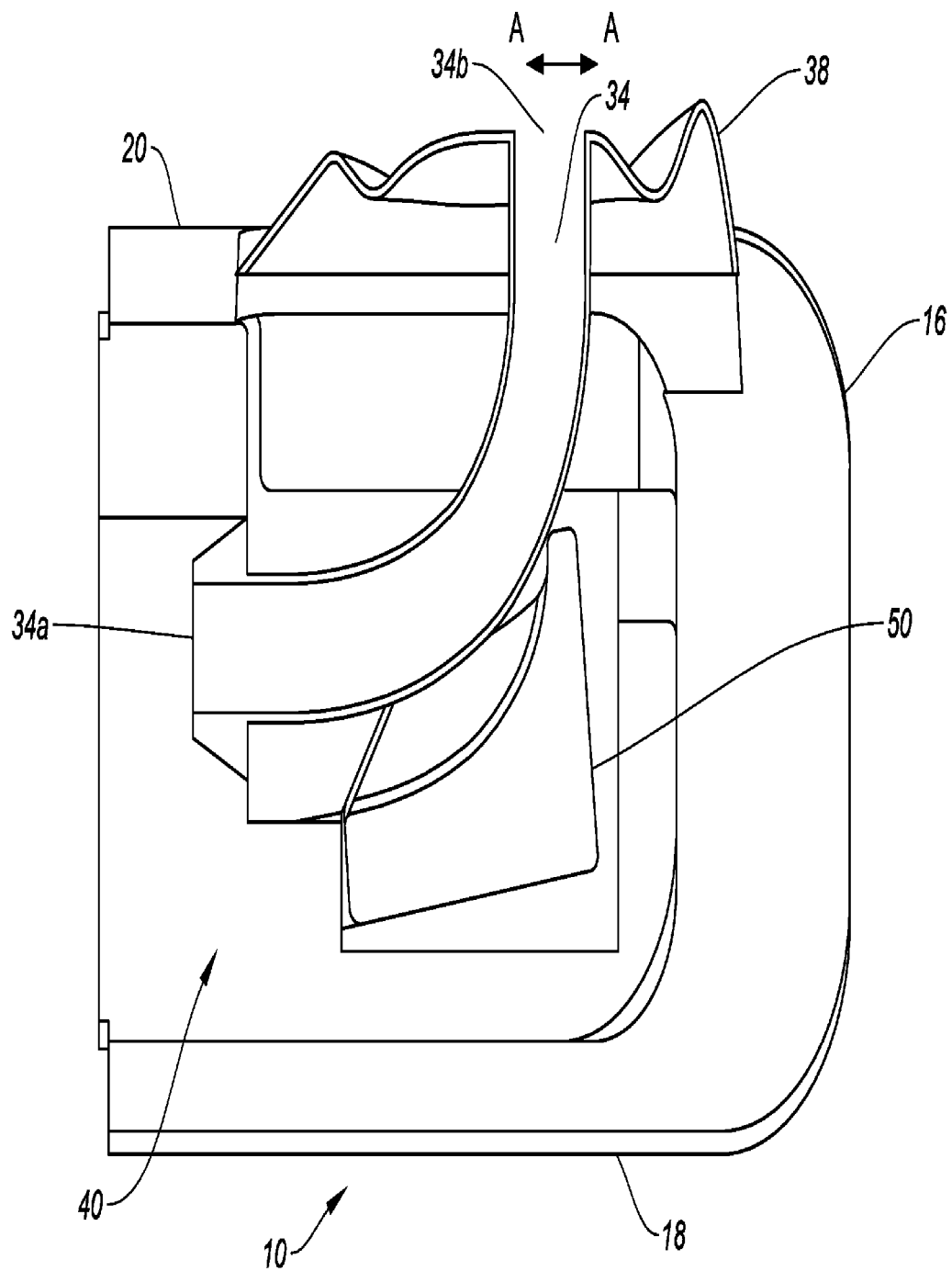
FIG. 5 is a cutaway side view of the coupler device and a duodenum scope of FIGS. 1A AND 1B in a first position.
Figure 6:
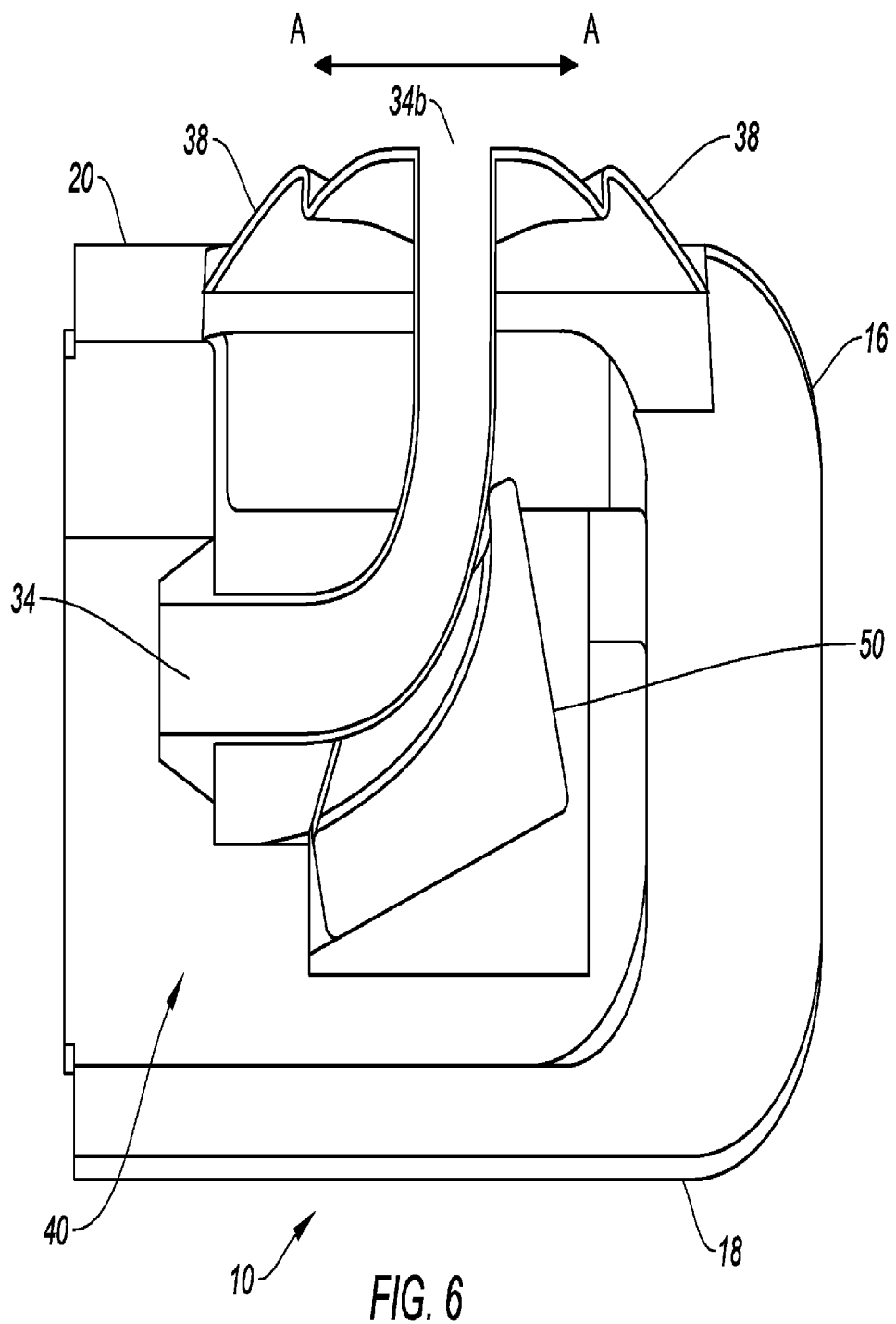
FIG. 6 is a cutaway side view of the coupler device and a duodenum scope of FIGS. 1A AND 1B in a second position.
Figure 7:
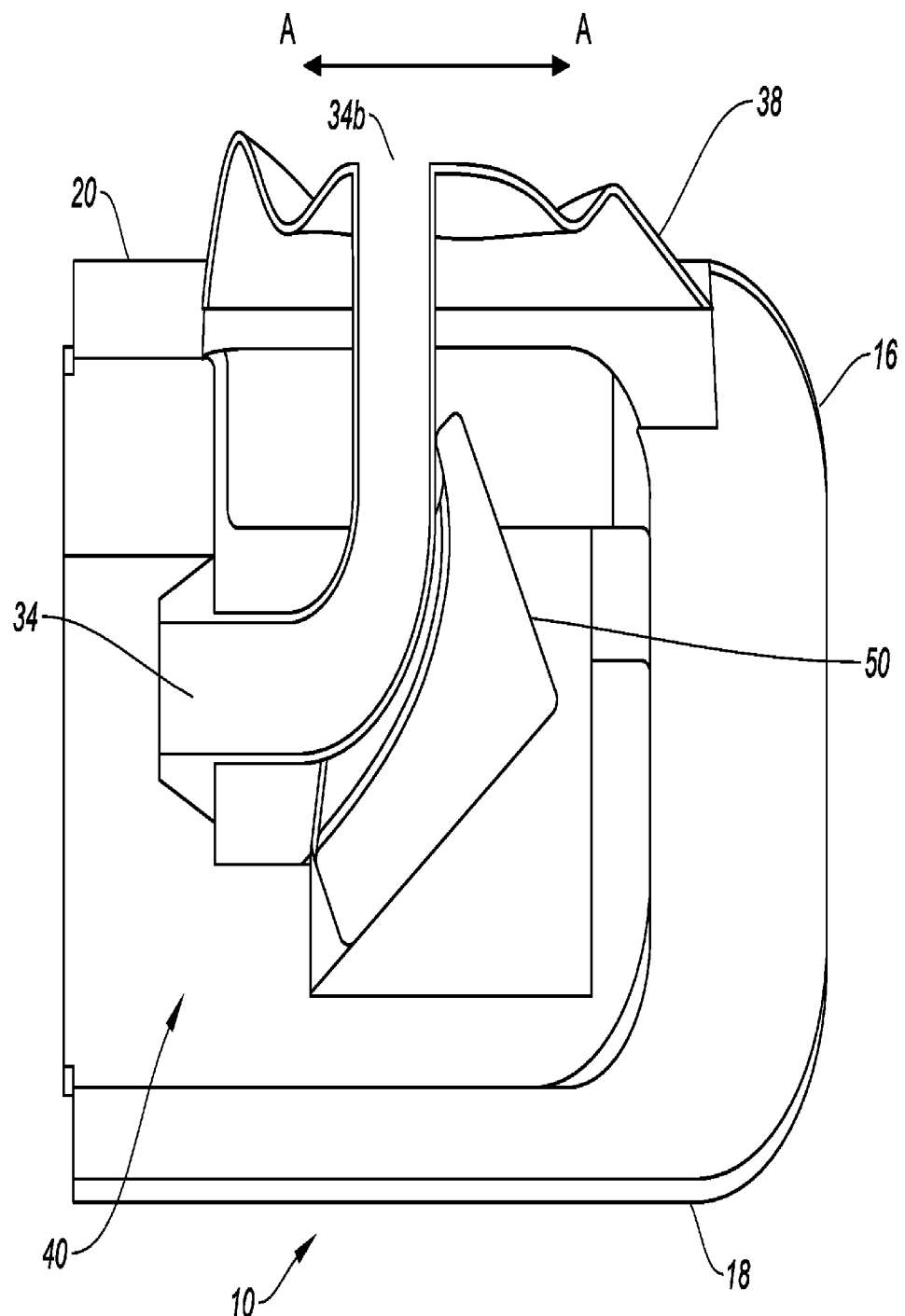
FIG. 7 is a cutaway side view of the coupler device and a duodenum scope of FIGS. 1A AND 1B in a third position.

As FIGS. 5 to 7 illustrate, in use when the elevator 50 of the scope 40 is actuated, the flexible working channel extension 34 of the coupler device moves or adjusts to this actuation, along the direction A-A In FIG. 5, the elevator 50 is raised slightly, creating a hinged ramp or shoulder that pushes the working channel extension 34 a corresponding angle and shifts the exit portal or distal end 34b of the working channel extension to the left. In FIG. 6 the elevator is raised higher than in FIG. 5, such that the distal end 34b of working channel extension 34 is likewise shifted further to the left in comparison to FIG. 5, while FIG. 7 shows the elevator 50 raised even higher and the distal end 34b of working channel extension 34 moved to the left even further in comparison to FIGS. 5 and 6.

Figure 8:
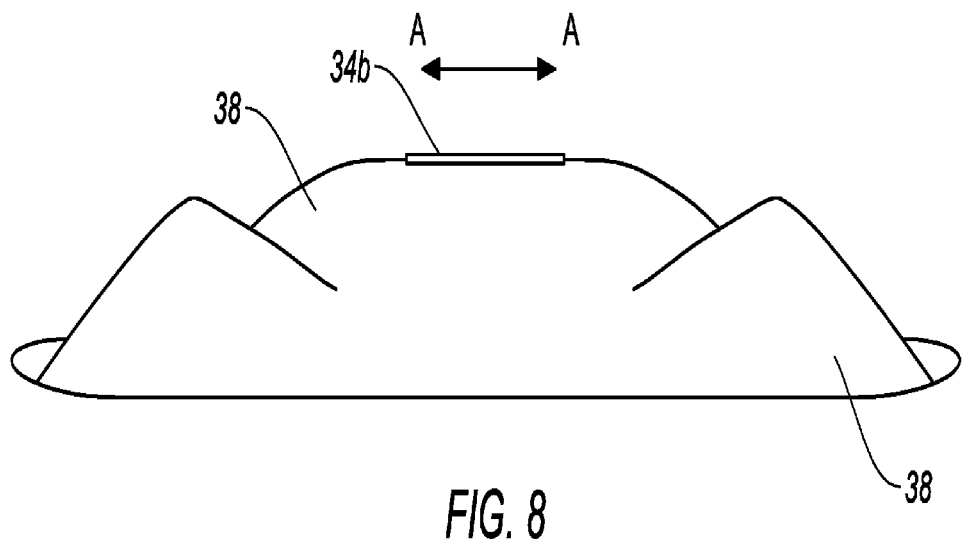
FIG. 8 is an enlarged side view of the working channel extension with membrane of the coupler device of FIGS. 1A AND 1B.

As FIG. 8 shows, the ability of the distal end 34b of working channel extension 34 to shift along the width of the working channel region 30 of the coupler device 10 is in part due to the fact that the distal end 34b is itself attached to a flexible membrane 38. This flexible membrane 38 comprises a plurality of loose folds or creases, allowing the excess material to stretch and bend as the elevator actuation forces the working channel extension to bend and shift in response. In addition, the flexible membrane 38 acts as a protective cover or hood for the working channel region 38, preventing the ingress of fluids, debris, or other unwanted matter from getting inside the scope 40 and causing a bacterial contamination or the infusion of other unwanted fluid, debris or particulate matter.

Figure 9:
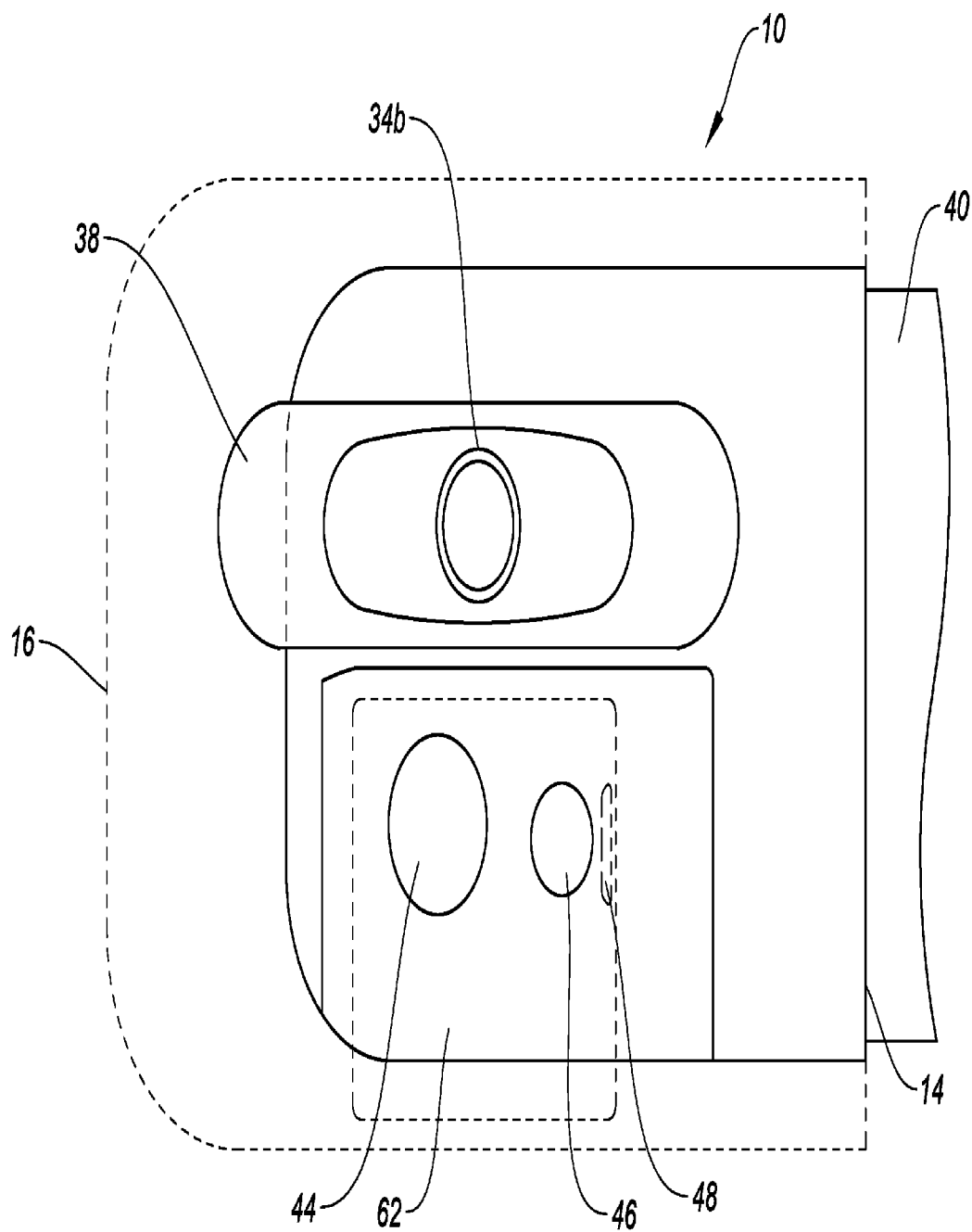
FIG. 9 is a top-down view of the coupler device of FIGS. 1A AND 1B.

It is contemplated that the coupler device 10 of the present disclosure may be configured for single, disposable use, or it may be configured for reuse. The coupler device 10 may be made of any biocompatible material, such as for example, silicone or another elastic or polymeric material. In addition, the material may be transparent. As shown in FIG. 9, the coupler device 10 may be formed of a transparent material to provide a transparent covering of the scope camera and light source, thereby allowing unhindered performance of the scope 40.

Figure 10:
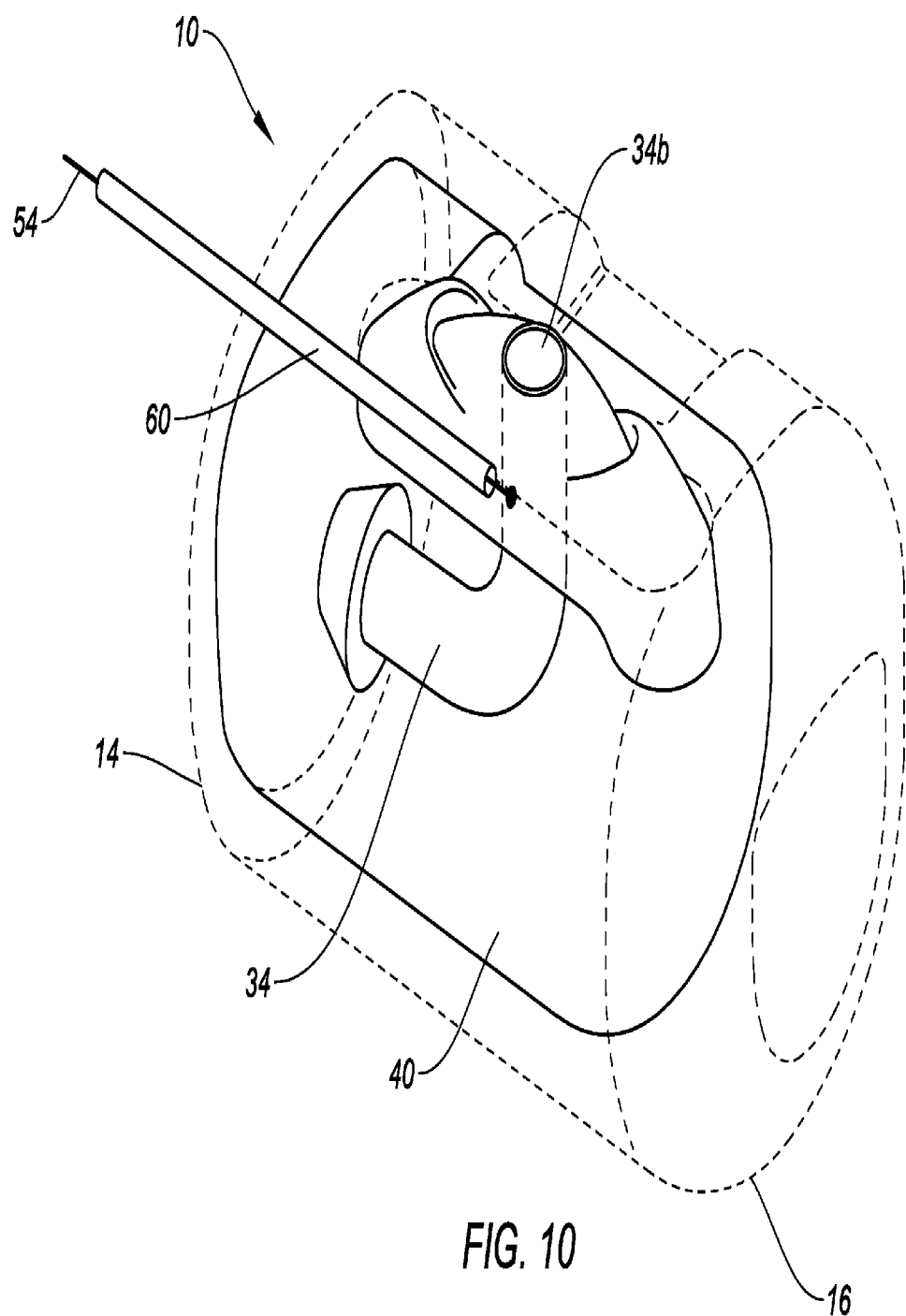
FIG. 10 is a cutaway view of another exemplary embodiment of a coupler device of the present disclosure.
Figure 11:
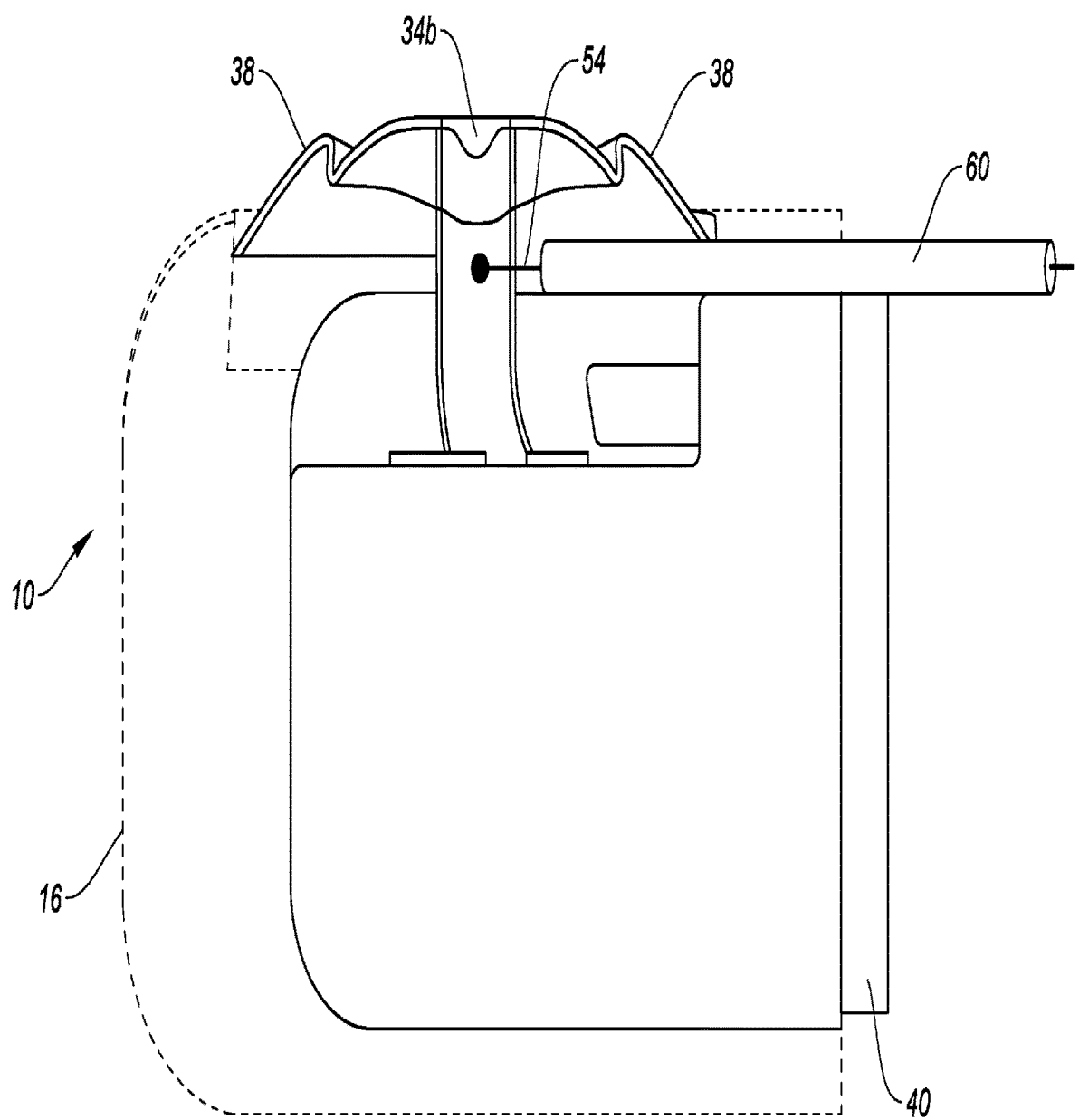
FIG. 11 is a cutaway side view of the coupler device of FIG. 10.
Figure 12:
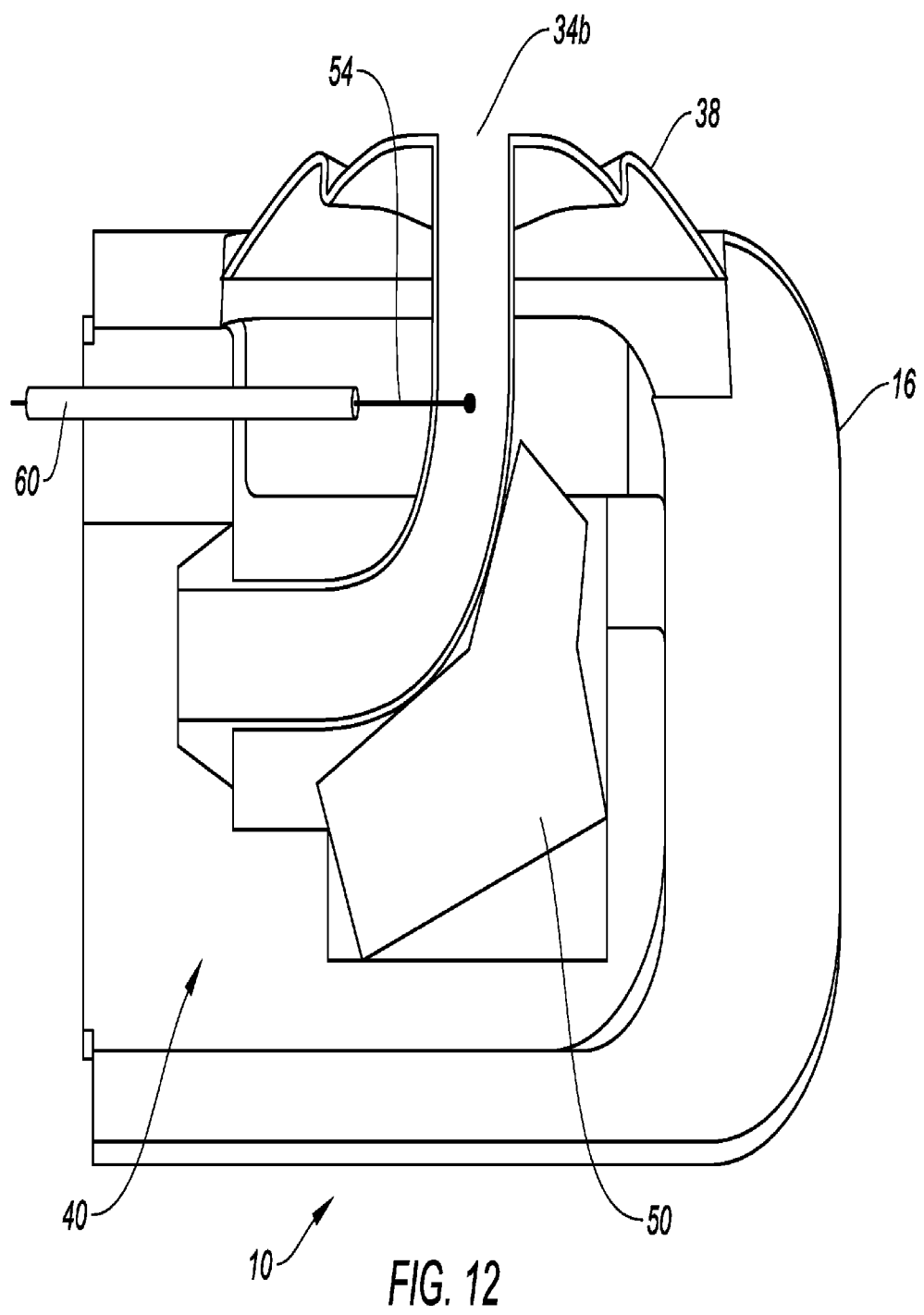
FIG. 12 is a cutaway side view of the coupler device of FIG. 10 in use with a duodenum scope.

FIGS. 10 to 12 show another exemplary embodiment of a coupler device 10 of the present disclosure. In this embodiment, the coupler device 10 is adapted for use with scopes that are actuated by cable and eliminates the need for the elevator component. As illustrated, the coupler device 10 maintains the same structural features as previously described, but now includes a further disposable external sheath 60 that can receive an interior actuating cable 54 of the scope. This cable 54 can be detached from the elevator and reattached to the flexible working channel extension 34 of the coupler device 10. The elevator is no longer needed in this embodiment, as actuation of the cable effects movement of the working channel extension 34. The external sheath 60 may be configured to attach directly to the scope 40, such as by winding around the outside of the scope or by a friction fit connection. In embodiments, multiple cables may be included in one or more sheaths to provide for articulation in other quadrants than the single axis articulation with elevators in current duodenoscopes.

In other embodiments, the coupler device 10 may also include a closable port (i.e., self-sealing) that allows for the injection of anti-adhesion, anti-bacterial, anti-inflammatory or other drug or infusible matter that prevents the adherence or colonization of bacteria on the scope. An applicator may be provided that is integrated into the coupler device 10 with a port for delivery of the infusible matter. Alternatively, the applicator may be separate from the coupler device 10 and applied to the distal end of the scope 40. The infusible matter may include forms of silver, including in a gel or other solution, platinum, copper, other anti-adhesion, anti-bacterial, anti-inflammatory or other drug or infusible matter that is compatible with the scope and coupler device materials and biocompatible for patient use.

In one exemplary embodiment, the device includes an anti-infective material. In another exemplary embodiment, the device includes an anti-infective coating. In still another embodiment, the device includes a coating that is hydrophobic. In yet another embodiment, the device is superhydrophobic. In even still another embodiment, the device is anti-infective and hydrophobic. Further yet in another embodiment, the device is anti-infective and superhydrophobic. In further still another exemplary embodiment, anti inflammatory coatings are incorporated into the device.

In one exemplary embodiment, the device 10 may include a silver ion coating. In another embodiment, the device 10 may have a silver hydrogel applied, infused, or made part of the device 10 in the area that covers or goes around the scope elevators. In addition to silver having antimicrobial properties, silver can also conduct electricity. Thus, in still another embodiment, the device 10 may include an electrical wire or other power transmission point to enable the creation of an electric field across the silver ion coating to improve the ability of the silver ion coating to prevent infection. In some embodiments, the electrical wire or other power transmission point may also apply to other antimicrobial and conductive materials, including platinum and copper.

Figure 13:
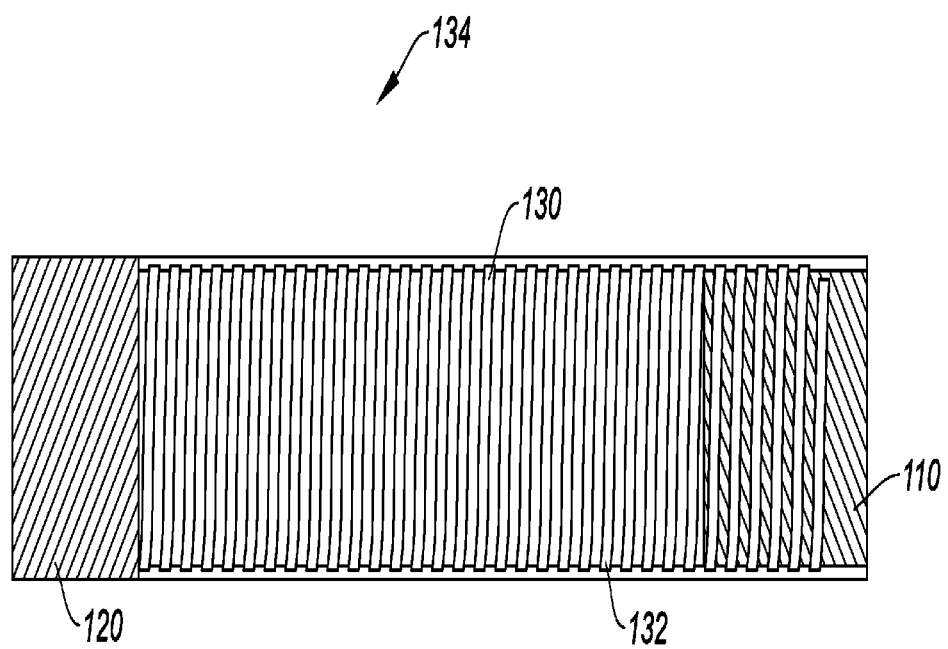
FIG. 13 is an enlarged side view of an exemplary embodiment of a working channel extension of the present disclosure.
Figure 14:
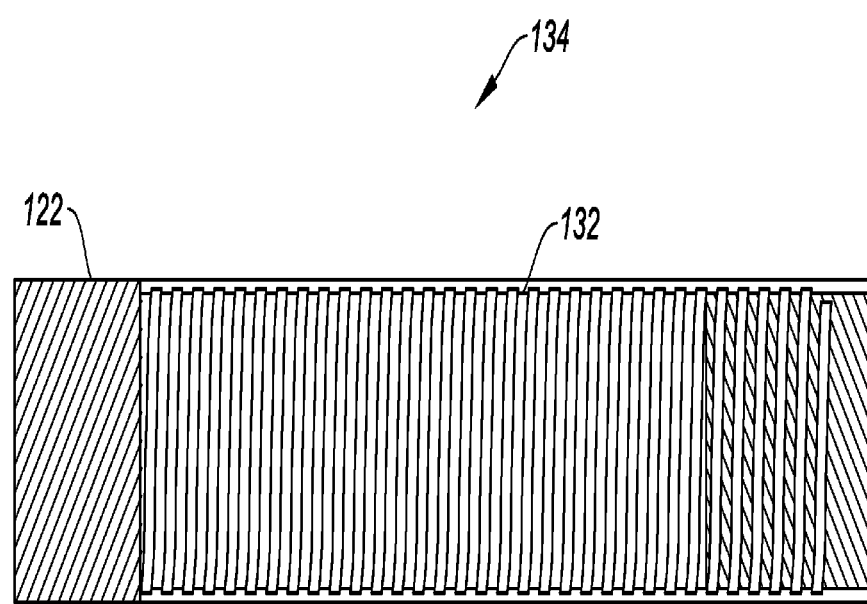
FIG. 14 is another enlarged side view of the working channel extension of FIG. 13

FIGS. 13 and 14 show another embodiment of the working channel extension 134 of the present disclosure. As contemplated, the working channel extensions may comprise a combination of different materials. For example, as shown in FIG. 13, the working channel extension 134 may be formed of multiple elastic materials joined to a biocompatible metal. In some embodiments, one of the elastic materials may be PTFE and another elastic material may be a biocompatible elastic material that covers the biocompatible metal. In the example of FIG. 13, the working channel extension 134 may comprise an inner elastic material 110 and an outer elastic material. The outside of the working channel extension 134 may embodiment, the biocompatible metal may be encapsulated by one or more of the elastic materials.

In FIG. 14, the outer biocompatible elastic material 120 is formed to create a gasket 122 to seal the proximal end of the working channel extension against 134 the working channel of an endoscope, creating a seal to prevent the intrusion of unwanted bacteria, biomatter and other material into this sealed area.

Figures 15A, 15B:
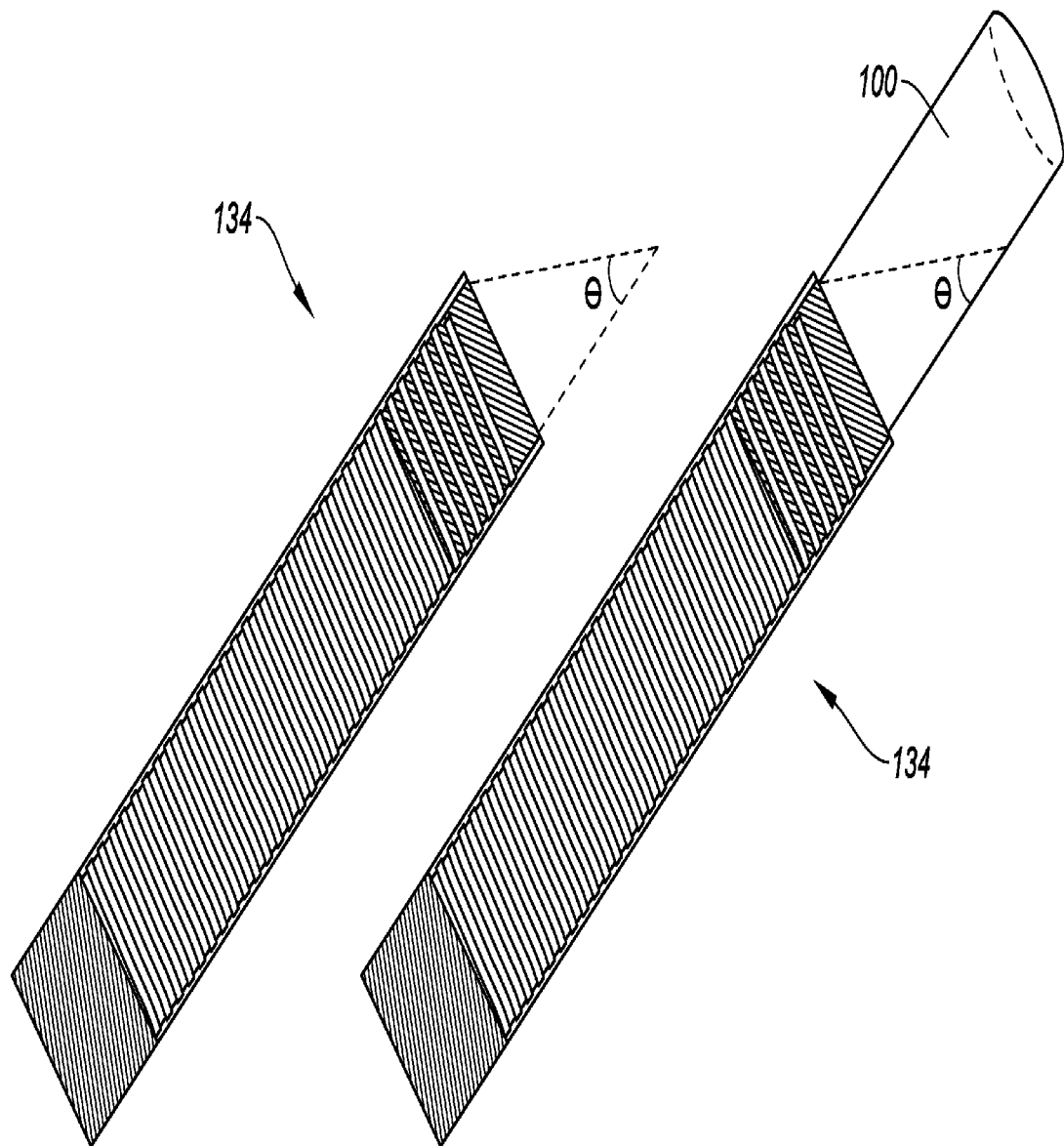
FIG. 15A is a perspective view of the working channel extension of FIG. 13
FIG. 15B shows the working channel extension of FIG. 15A in use with an instrument.

In FIG. 15A, a working channel extension 134 is shown with an adjustable angle of exit 8 for locking an instrument 100 in place. In this embodiment, when the angle of exit 8 is adjusted, it creates compressive force in the working channel 134, locking an instrument 100 in place, as shown in FIG. 15B. This can be used to fixate an instrument while a wire is advanced through the instrument, or to fixate a wire, while a second instrument is exchanged over the wire.

Figure 16:
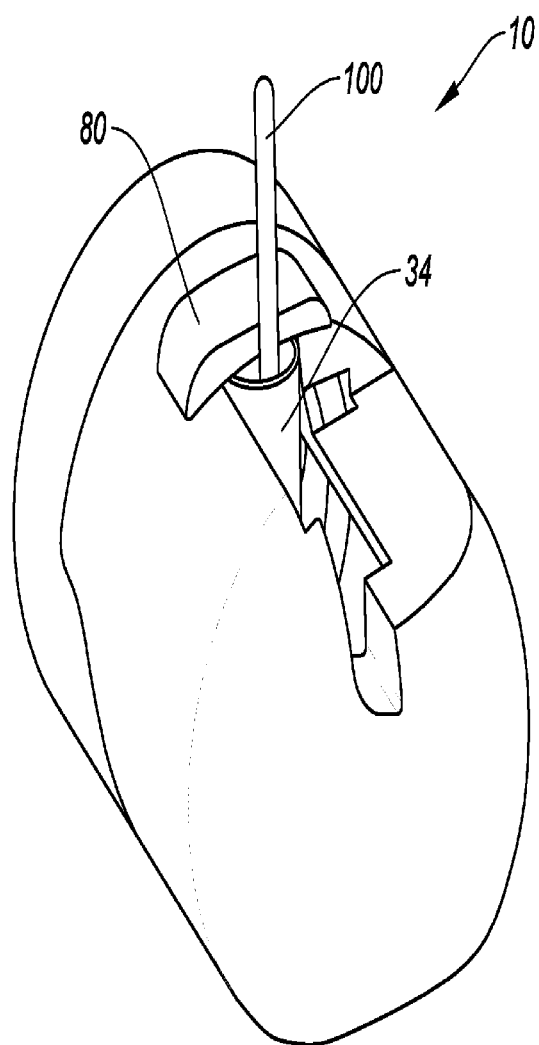
FIG. 16 is a perspective top-down view of the coupler device of FIG. 1A with a locking feature.

In FIG. 16, an alternative embodiment is shown for locking an instrument I 00 in place. In this embodiment, the working channel extension 134 is raised to a point in which the instrument 100 in the working channel extension 134 is compressed against a lock 80 on the device 10, causing a change in the angle of exit of the working channel extension 134 and locking the instrument 100 in a fixated place in the working channel extension 134.

Figure 17:
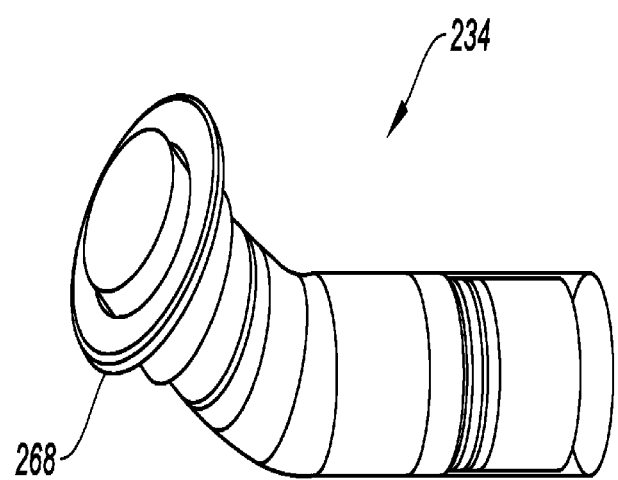
FIG. 17 is a perspective view of another exemplary embodiment of a working channel extension of the present disclosure.

In FIG. 17, an alternative embodiment of the working channel extension 234 is shown with a flange 268 for attaching the working channel extension to the membrane material 38 that is part of the device 10.

Other embodiments will be apparent to those skilled in the art from consideration of the specification and practice of the embodiment disclosed herein. It is intended that the specification and examples be considered as exemplary only, with a true scope and spirit of the embodiment being indicated by the following claims.

What is claimed is:

1. A device for use with an endoscope having an elongate shaft with an internal working channel, the device comprising:
   a sheath;
   a main body comprising a visualization section for allowing viewing of tissue by the endoscope and a proximal end configured for attachment to a distal end portion of the endoscope;
   a passage within the main body having an exit portal and a proximal end configured for alignment with the working channel of the endoscope;
   a flexible membrane in contact with, and coupled to, an outer surface of the main body and at least partially surrounding the exit portal; and
   wherein the device is configured such that an instrument passing through the passage is capable of angular adjustment relative to the main body by actuation of the endoscope.

2. The device of claim 1, wherein the passage comprising a working channel extension within the main body.

3. The device of claim 2, wherein the working channel extension is flexible and capable of angular adjustment by actuation of the endoscope.

4. The device of claim 1, wherein the proximal end of the passage is configured for insertion into the working channel of the endoscope.

5. The device of claim 1, wherein the main body of the device is configured to accommodate therein an elevator for angular adjustment of the instrument.

6. The device of claim 1, further comprising a mechanism for articulating an instrument passing through the passage.

7. The device of claim 1, wherein the main body comprises an elastic or elastomeric material.

8. The device of claim 1, wherein the endoscope is a side-viewing scope.

9. The device of claim 1, wherein the endoscope includes an elevator for angular adjustment of the instrument.

* * * * *